US00PP14756P3

(12) United States Plant Patent
Murakami

(10) Patent No.: US PP14,756 P3
(45) Date of Patent: May 4, 2004

(54) PETUNIA PLANT NAMED 'SUNBELRE'

(50) Latin Name: *Petunia hybrida*
Varietal Denomination: Sunbelre

(75) Inventor: Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/327,030

(22) Filed: Dec. 24, 2002

(65) Prior Publication Data

US 2003/0131392 P1 Jul. 10, 2003

(30) Foreign Application Priority Data

Dec. 28, 2001 (JP) ..... 14311

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

Disclosed herein is a new and distinct variety of Petunia plant having a semi-decumbent growth habit. The Petunia plant has abundant branching, particularly with respect to secondary branching, and forms a great profusion of blooms with the entire plant remaining in bloom for a considerable period of time. The flowers are single and very small. The petal coloration is deep red. The base color of the corolla throat is vivid greenish-yellow and the outside of the corolla tube is olive-gray. The plant exhibits high resistance to rain, heat, drought and diseases, such as Powdery Mildew.

2 Drawing Sheets

Botanical/commercial classification: Petunia hybrida/Petunia Plant.
Varietal denomination: cv. 'Sunbelre'.

BACKGROUND OF THE VARIETY

The Petunia is a very popular plant that is used for flower bedding and potting in the summer season. There are only a few small-flowered Petunia varieties, such as 'Suntory SP-R' (U.S. Plant Pat. No. 9,557), 'Sunberubu' (U.S. Plant Pat. No. 9,754), 'Sunbelchipi' (U.S. Plant Pat. No. 10,355), and 'Sunbeluki' (U.S. Plant Pat. No. 11,558) that are of the semi-decumbent type, possess a medium plant height with abundant branching, and possess a high resistance to heat and rain and disease. Accordingly, this invention was aimed at obtaining a new Petunia variety having deep red petals, and very small flowers combined with the above features.

The new variety of Petunia plant according to this invention originated by crossing the 'Sunbelchipi' variety as female parent (U.S. Plant Pat. No. 10,355) and a Petunia variety named 'R5' as male parent.

The crossing was conducted during May 1997 at the Omi R & D Center of SUNTORY Ltd., located at 863-1, Aza-Iketani, Omori-cho, Youkaichi-shi, Shiga-ken, Japan. From this crossing 50 seedlings were obtained and 5 seedlings were selected in view of their semi-erect growth habit and petal coloration by the end of September 1998. These 5 seedlings were grown and were evaluated during potting and bedding trials. One plant of the present invention was selected during September 1999. The selected plant was propagated by the use of cuttings and was grown in a trial in pots in greenhouses and in the field at the Omi R & D Center from April to November 2000. The botanical characteristics of the selected plant were examined, using the similar 'Sunbelchipi' variety (U.S. Plant Pat. No. 10,355) for comparison. As a result, it was concluded that this new Petunia plant is distinguishable from any other variety, whose existence is known to me, and is uniform and stable in its characteristics. The new Petunia variety of the present invention has been named 'Sunbelre'.

The new variety of the present invention can be readily distinguished from the 'Sunbelrikupi' variety (U.S. Plant patent application Ser. No. 10/327,017, filed Dec. 24, 2002) and the 'Sunbelkos' variety (U.S. Plant patent application Ser. No. 10/326,967, filed Dec. 24, 2002) through an observation of the flower coloration. Each of these varieties had the same female parent. The new 'Sunbelre' variety of the present invention forms deep red flowers, the 'Sunbelrikupi' variety forms vivid reddish-purple flowers, and the 'Sunbelkos' variety forms deep purplish-pink flowers with a dark red center.

In the following description, the color information is in accordance with The R.H.S. Colour Chart of The Royal Horticultural Society, London, England. A color chart based on The Japan Color Standard for Horticultural Plants (J.H.S. Color Chart) is also added for reference.

The main botanical characterisitics of the 'Sunbelchipi' female parent are as follows:

Plant:
- *Growth habit.*—Semi-decumbent.
- *Plant height.*—Approximately 15–16 cm.
- *Spreading area of plant.*—The stem extends to length of approximately 11–13 cm from the base.
- *Blooming period.*—April to late October in the southern Kanto area, Japan. The plant shape does not change throughout this period.

Stem:
- *Thickness.*—Approximately 2–3 mm.
- *Pubescence.*—Present.
- *Branching.*—Abundant with a superior branching propensity, especially with respect to secondary branches.
- *Length of internode.*—Approximately 1.4 cm.

Leaf:
- *Shape.*—Lanceolate.
- *Length.*—Approximately 5.1 cm.
- *Width.*—Approximately 1.6 cm.
- *Color.*—Dark yellow-green (R.H.S. 146A, J.H.S. 3508).
- *Thickness.*—Approximately 0.2–0.4 mm.
- *Pubescence.*—Sparse.
- *Leaf attachment angle to stem.*—Slanted upward to horizontal.

Flower:
- *Facing direction.*—Horizontal.
- *Type.*—Single.
- *Shape.*—Funnel-shaped, with five fissures.
- *Shape of petal tip.*—Round.
- *Waviness of petal.*—Weak.
- *Lobation of petal.*—Shallow.
- *Diameter.*—Approximately 2.8–2.9 cm.
- *Color.*—Petal: Vivid purplish-red (R.H.S. 57C, J.H.S. 9707). Bottom color of corolla throat: Strong yellow (R.H.S. 9A, J.H.S. 2513). Outside color of corolla tube: Light greenish-yellow (R.H.S. 5C, J.H.S. 2904).
- *Reproductive organs.*—1 normal pistil and 5 normal stamens.
- *Fertility.*—Fertile, but self-incompatible.
- *Peduncle.*—Approximately 0.7–0.8 mm in thickness, and approximately 1.9 cm in length.
- *Physiological and ecological characteristics.*—High resistance to heat, rain, drought and diseases, such as Powdery Mildew. The resistance to heat and rain is very strong.
- *Blooming.*—A bloom commonly lasts approximately 10 days on the plant. Pinching is not necessary to ensure continuous blooming; however, it does tend to enhance bloom production.

The main botanical characteristics of the 'R5' male parent are as follows:

Plant:
- *Growth habit.*—Semi-erect.
- *Plant height.*—Approximately 20 cm.
- *Spreading area of plant.*—The stem extends to length of approximately 5 cm from the base.
- *Blooming period.*—April to October in the southern Kanto area, Japan. The plant shape does not change throughout this period.

Stem:
- *Thickness.*—Approximately 2.4 mm.
- *Pubescence.*—Sparse.
- *Branching.*—Abundant with a superior branching propensity, especially with respect to secondary branches.
- *Length of internode.*—Approximately 1.3 cm.

Leaf:
- *Shape.*—Lanceolate.
- *Length.*—Approximately 3.4 cm.
- *Width.*—Approximately 1.1 cm.
- *Color.*—Dark olive-green (R.H.S. 137A, J.H.S. 3707).
- *Thickness.*—Approximately 0.5 mm.
- *Pubescence.*—Sparse.
- *Leaf attachment angle to stem.*—Horizontal to droopy.

Flower:
- *Facing direction.*—Upward to slanted upward.
- *Type.*—Single.
- *Shape.*—Funnel-shaped, with five fissures.
- *Shape of petal tip.*—Round.
- *Waving of petal.*—Weak.
- *Lobation of petal.*—Shallow.
- *Diameter.*—Approximately 2.9 cm.
- *Color.*—Petal: Vivid reddish-orange (R.H.S. 33A, J.H.S. 0705) ground color with vivid red streaking (R.H.S. 44A, J.H.S. 0707) and a grayish-red central area (R.H.S. 177A, J.H.S. 0419). The base color of corolla throat: Vivid yellow-orange (R.H.S. 15A, J.H.S. 2205). The outside color of corolla tube: Brilliant yellow-orange (R.H.S. 15C, J.H.S. 2204).
- *Reproductive organs.*—1 normal pistil and 5 normal stamens.
- *Fertility.*—Fertile, but self-incompatible.
- *Peduncle.*—Approximately 0.8 mm in thickness, and approximately 2.0 cm in length.
- *Physiological and ecological characteristics.*—High resistance to heat, rain, drought and diseases, such as Powdery Mildew. The resistance to heat and rain is very strong.
- *Blooming.*—A bloom commonly lasts approximately 10 days on the plant. Pinching is not necessary to ensure continuous blooming; however, it does tend to enhance bloom production.

SUMMARY OF THE VARIETY

This new variety of Petunia plant 'Sunbelre' has a semi-decumbent growth habit with abundant branching, and forms single and very small deep red flowers in a great profusion with the entire plant remaining in bloom for a considerable period of time. The plant has high tolerances to cold and heat, high resistance to pests and diseases, particularly Powdery Mildew, and high resistance to rain.

The plants described and depicted herein were propagated by the use of cuttings and were approximately ten months of age. Such cuttings were placed in a greenhouse in January, were transplanted in February, were further transplanted to pots in April and were thereafter placed outdoors, and were trimmed during August. When present in a greenhouse, the plants were grown under controlled greenhouse conditions under full sunshine with no shielding from light. The minimum greenhouse temperature was maintained above 13° C.

BRIEF DESCRIPTION OF THE PHOTOGRAPHS

The depicted plants had been reproduced by the use of cuttings and were photographed during October while growing outdoors in pots at an age of approximately ten months at Youkaichi-shi, Shiga-ken, Japan.

DESCRIPTION OF THE NEW VARIETY

Figure 1:
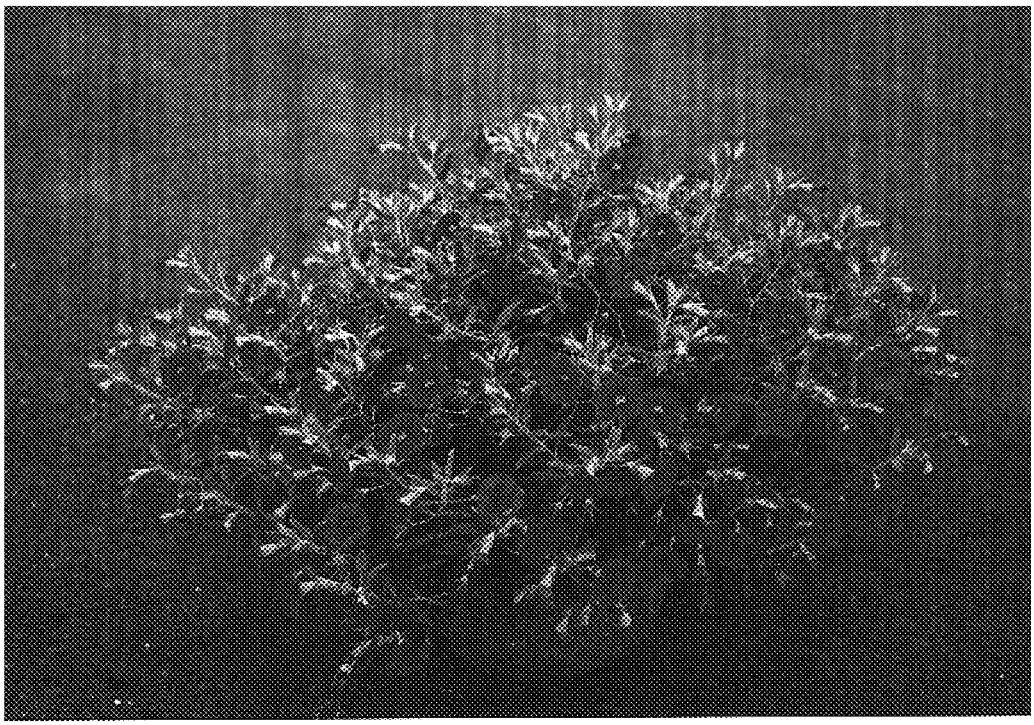
FIG. 1 illustrates the overall growth habit of the new variety of Petunia plant 'Sunbelre' while flowering.
Figure 2:
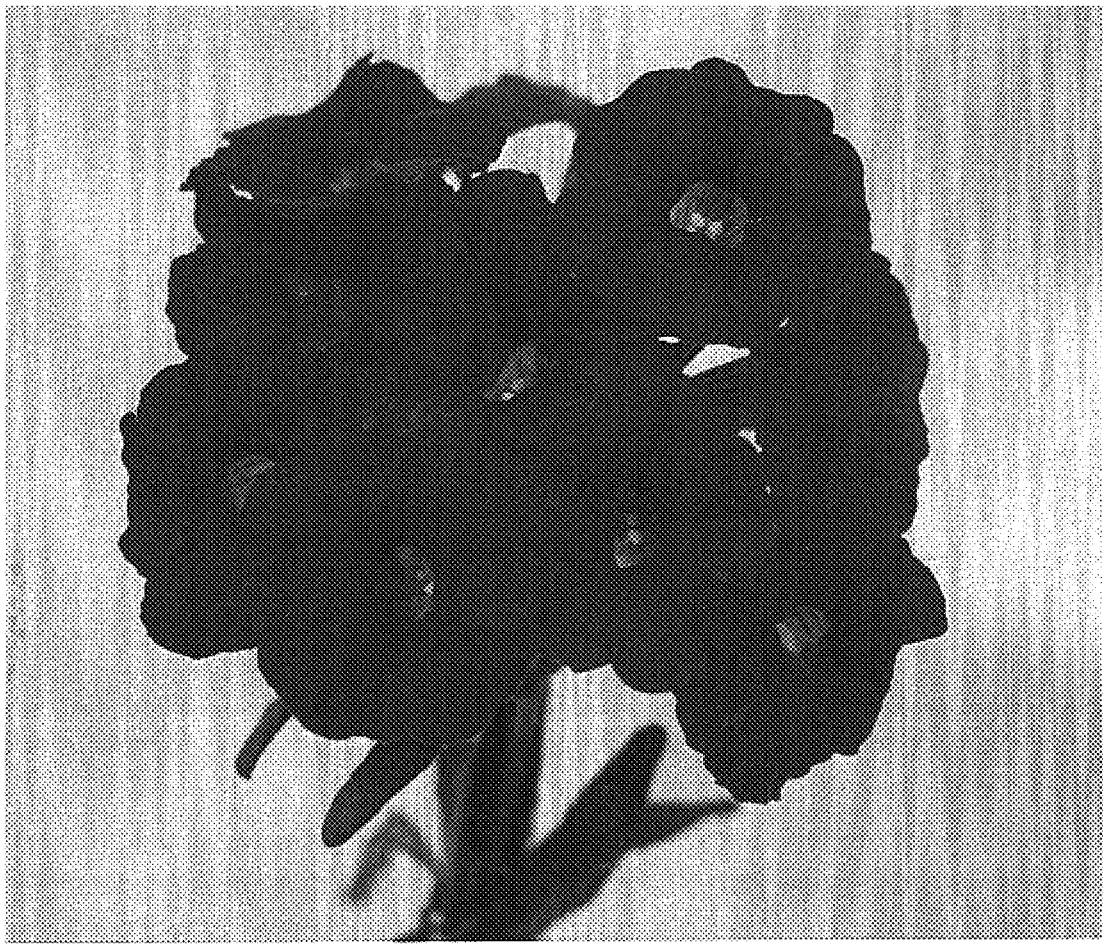
FIG. 2 illustrates a close view of the flowers and foliage of the new variety of Petunia plant 'Sunbelre'.

The botanical characteristics of the new and distinct variety of Petunia plant named 'Sunbelre' are as follows when observed during October at Yokaichi-shi, Shiga-ken, Japan:

Plant:

*Growth habit.*—Semi-decumbent.

*Plant height.*—Approximately 14 cm.

*Spreading area of plant.*—The stem extends to length of approximately 8 cm from the base.

*Blooming period.*—April to late October in the southern Kanto area, Japan. The plant shape does not change throughout this period.

Stem:

*Thickness.*—Approximately 2.4 mm.

*Pubescence.*—Sparse.

*Branching.*—Abundant with superior branching, especially with respect to secondary branches.

*Length of internode.*—Approximately 1.3 cm.

Leaf:

*Shape.*—Lanceolate.

*Length.*—5.2 cm.

*Width.*—1.2 cm.

*Color.*—Moderate olive-green (R.H.S. 147A, J.H.S. 3509) on the upper surface and R.H.S. 146B on the lower surface.

*Venation.*—Pinnate and R.H.S. 146B.

*Texture.*—Smooth.

*Margin.*—Entire.

*Thickness.*—Approximately 0.6 mm.

*Pubescence.*—Sparse.

*Leaf attachment angle to stem.*—Slanted upward to horizontal.

Flower:

*Facing direction.*—Horizontal.

*Type.*—Single.

*Shape.*—Funnel-shaped, with five fissures.

*Shape of petal tip.*—Round.

*Waviness of petal.*—Weak.

*Lobation of petal.*—Shallow.

*Diameter.*—Approximately 2.8 cm.

*Color.*—Petal: Deep red (R.H.S. 46A, J.H.S. 0408). Base color of corolla throat: Vivid greenish-yellow (R.H.S. 153D, J.H.S. 2706). Outside color of corolla tube: Brilliant greenish-yellow (R.H.S. 8A, J.H.S. 2704).

*Venation.*—R.H.S. 59B in coloration, and generally radiates linearly outwardly from the center with much branching.

*Sepals.*—R.H.S. 144A on the upper surface and R.H.S. 144B on the lower surface, generally lanceolate in configuration, with an entire margin, approximately 11.5 mm in length, approximately 2.5 mm in width at the widest point, and five in number. The calyx is tubular and divides into five sepals.

*Reproductive organs.*—1 normal pistil and 5 normal stamens. The stigma is club-shaped and R.H.S. N144C in coloration. The style is approximately 9 mm in length and R.H.S. 145B in coloration. The ovary is R.H.S. N144D in coloration. The stamens commonly are of variable lengths from approximately 8.5 to 11.5 mm. Pollen is formed in a quantity that is typical of *Petunia hybrida* and is near R.H.S. 17A in coloration.

*Fertility.*—Fertile, but self-incompatible.

*Seeds.*—R.H.S. N186A in coloration, approximately 0.6 mm in diameter, and generally round. The quantity is typical of *Petunia hybrida.*

*Peduncle.*—Approximately 0.8 mm in thickness, and approximately 1.9 cm in length. R.H.S. 177A on the upper side and R.H.S. 144B on the lower side. The texture is smooth.

*Physiological and ecological characteristics.*—High resistance to heat, rain, drought and diseases such as Powdery Mildew. The resistance to heat and rain is very strong.

*Blooming.*—A bloom commonly lasts approximately 10 days on the plant. Pinching is not necessary to ensure continuous blooming; however, it does tend to enhance bloom production.

This new variety of Petunia plant is most suitable for flower bedding and potting, particularly in hanging pots or in planters, and is excellent for use as a ground cover. Pinching of old blossoms will enhance the formation of new blossoms.

I claim:

1. A new and distinct variety of Petunia plant, substantially as herein illustrated and described, characterized particularly as to novelty by (A) having a semi-decumbent growth habit, (B) a great profusion of blooms with the entire plant remaining in bloom for a considerable period of time, (C) flowers that are single and very small, having deep red petals have a deep red color, and (D) a high resistance to rain, heat, drought and pests.

* * * * *